US007166438B2

(12) United States Patent
Patchev et al.

(10) Patent No.: US 7,166,438 B2
(45) Date of Patent: Jan. 23, 2007

(54) IN VITRO SCREENING FOR LIGANDS OF THE ESTROGEN RECEPTOR

(75) Inventors: Vladimir Patchev, Jena (DE); Youriy Mitev, Jena (DE); Siegmund Wolf, Jena (DE); Gernot Langer, Berlin (DE)

(73) Assignee: Schering AG, Berlin (DE)

( * ) Notice: Subject to any disclaimer, the term of this patent is extended or adjusted under 35 U.S.C. 154(b) by 730 days.

(21) Appl. No.: 09/989,952

(22) Filed: Nov. 20, 2001

(65) Prior Publication Data

US 2003/0087303 A1    May 8, 2003

(30) Foreign Application Priority Data

Nov. 7, 2001 (EP) .................................. 01126336

(51) Int. Cl.
G01N 33/53 (2006.01)
(52) U.S. Cl. ....................................... 435/7.8; 435/7.1
(58) Field of Classification Search .................. 435/7.1
See application file for complete search history.

(56) References Cited

FOREIGN PATENT DOCUMENTS

| WO | 99/11760    | 3/1999 |
| WO | 99/18124    | 4/1999 |
| WO | 99 41608 A  | 8/1999 |
| WO | 99/42108    | 8/1999 |
| WO | 99 42108 A  | 8/1999 |
| WO | 00 26232 A  | 5/2000 |
| WO | 00/37681    | 6/2000 |

OTHER PUBLICATIONS

V. Patchev et al: "Steroid Hormone-Dependent Organization of . . . ", R. G. Landes Company, Austin, 1999.
S.E. Alves et al: "Estrogen and Barain Function . . . ", m. oETTEL and e. Schillinger, Eds., Estrogens and Antiestrogens, Handbook of Experimental Pharmacology, vol. 135/I, Springer, Berlin, Heidelberg, 1999, pp. 315-328.
Vincent Giguere et al: "Estrogen Receptor B: Re-Evaluation of Estrogen . . . ", Steroids vol. 63, pp. 335-339, 1998.
George G.J.M. Kuiper: "The Novel Estrogen Receptor-B Subtype: Potential Role in the Cell . . . "FEBS 18558, FEBS Letters 410 (1997), pp. 87-90.
Paul J. Shughrue, et al: "Comparative Distribution of Estrogen Receptor-A . . . " The Journal of Comparative Neurology, vol. 388, pp. 507-525, 1997.
Sergio A. Onate et al: "Sequence and Characterization of a Coactivator for the Steroid Hormone . . . " Science, vol. 270, Nov. 1995, pp. 1354-1357.
Daniel Robyr et al: "Nuclear Hormone Receptor Coregulators . . . ", Molecular Endocrinology, vol. 14, pp. 329-347, 2000.
Els M.J.J. Berns et al: "Predictive Value of SRC-1 for Tamoxifen Response . . . ", Breast Cancer Research and Treatment, vol. 48, pp. 87-92, 1998.

Simon P. Newman et al: "Cofactor Competition Between the Ligand-Bound Oestrogen Receptor and . . . " Oncogene 2000, vol. 19, pp. 490-497.
Fernand Labrie et al: "EM-652 (SCH 57068), A Third Generation Serm . . . " Journal of Steroid Biochemistry and Molecular Biology, Vol. 69, 1999, pp. 51-84.
Jianming Xu et al: "Partial Hormone Resistance in Mice with Disruption . . . " Science, vol. 279, Mar. 20, 1998, pp. 1922-1925.
O.C. Meijer et al: "Differential Expression and Regional Distribution of . . . " Endocrinology, vol. 141, No. 6, pp. 2192-2199., 2000.
Xiu Fen Ding et al: "Nuclear Receptor-Binding Sites of Coactivators . . . ", Molecular Endocrinology, 1998, 12 (2), pp. 302-313.
Yasutomi Kamei et al: "A CBP Integrator Complex Mediates . . . " Cell, Vo. 86, pp. 403,414, May 3, 1996.
Chelby L. Berger et al: "Guide to Molecular Cloning Techniques", Methods in Enzymology, vol. 152, pp. 709-713, 1987.
Harvey J. Whitfield et al: "Optimization of CRNA Probe . . . " Cellular and Molecular Neurobiology, vol. 10, No. 1, 1990, pp. 145-157.
Gaochao Zhou et al: "Nuclear Receptors Have Distict Affinities for Coatovators . . . " Molecular Endocrinology, vol. 12, pp. 1594-1604, 1998.
Lascombe, L, et al: "Estrogenic Activity Assessment of . . . ", Environmental Health Perspectives, vol. 108, No. 7, Jul. 2000, pp. 621-629.
Hanstein, B., et al: "Functional Analysis of a Novel Estrogen . . . ", Molecular Endocrinology, vol. 13, No. 1, Jan. 1999, pp. 129-137.
Zhou, G., "Nuclear Receptors Have Distinct Affinities for Coativators . . . ", Molecular Endocrinology, Baltimore, MD, US, vol. 12, No. 10, Oct. 1998, pp. 1594-1604.
Martini, P., et al: "Prothymosin Alpha Selectively Enhances Estrogen Receptor . . . " Molecular and Cellulae Biology, vol. 20, No. 17, Sep. 2000, pp. 6224-6232.
Stenoien, D., et al: "Ligand-Mediated Assembly and Real-Time Cellular Dynamics . . . " Molecular and Cellular Biology, vol. 21, No. 13, Jul. 2001, pp. 0270-7306.
L. W. Swanson: Brain Maps:Structure of the Rat Brain, A Laboratory Guide with Printed and Electronic Templates for Data, Models and Schematics, Amsterda, Lausanne . . . , 1998.

Primary Examiner—Michael Pak
(74) Attorney, Agent, or Firm—Michael J. Striker

(57) ABSTRACT

A method for in vitro screening a group of test substances for a ligand using two assay systems, i.e. a cellular or tissue assay system and an enzymatic assay system, is described. First, those test substances are selected which have transcriptional ER-mediated activity measured by an ER-driven reporter gene in the cellular or tissue assay system with an $EC_{50(ER)}$(half-maximally effective ligand concentration) lower than or equal to 10 nmol/l. Then in an enzymatic assay system the selected test substances having the required transcriptional ER-mediated activity are tested by measuring a physical-chemical interaction (recruitment) of SRC-1 and the ER in the presence of the test substances. The selected ligand activates the ER and induces interaction with the co-present SRC-1 with an $E_{50(ER+SRC)}$ higher than or equal to 100 nmol/l. The ligands found by the inventive screening method are useful for treatment and prevention of neurodegeneration in the cerebral cortex, especially of age-related cognitive disorders, affective disorders, Alzheimer's diseases and cerebral ischemia/stroke.

2 Claims, No Drawings

IN VITRO SCREENING FOR LIGANDS OF THE ESTROGEN RECEPTOR

INTRODUCTION

The invention relates to an in vitro method for detecting ligands and in vitro screening for ligands of the estrogen receptor having neurotropic and minimal systemic estrogen-like properties. The invention further relates to an in vitro use of a steroid receptor coactivator-1 (SRC-1) for detecting ligands of the estrogen receptor having defined properties.

STATE OF THE ART

Substances which Have Neurotropic Functions without Affecting other Estrogen-Sensitive Organs The international application WO 99/42108 of PATCHEV et al. describes steroids as medication for selectively supplementing estrogen deficiency in the central nervous system without influencing other organs or systems. Such compounds (ligands) have selective neurotropic properties; they do not affect other estrogen-sensitive organs. The selective neurotropic effect on the nervous system was tested in animal models.

The desired profile of drugs for the treatment of symptoms of estrogen deficiency in the central nervous system requires that these drugs act on estrogen-dependent target genes in the brain while having only minor effects or no effect in estrogen-sensitive organs of the reproductive system (e.g., endometrium, breast, pituitary).

Estrogens have a large number of effects on the central nervous system (CNS). Mental effects of estrogens result in irreversible "hard-wiring" of neuronal circuits which determine several aspects of brain function [V. K. Patchev and O. F. X. Almeida, Steroid hormone-dependent organization of neuroendocrine functions, R.G. Landes Company, Austin, 1999]

In the mature brain, physiological levels of estrogens, derived from the gonads, influence control of reproductive functions as well as brain activities which are not related to reproduction and sexual behavior, such as learning, memorization, spatial orientation, emotionality and processing of cognitive information [S. E. Alves and B. S. McEwen, Estrogen and brain function: Implications for aging and dementia; in M. Oettel and E. Schillinger, eds., Estrogens and Antiestrogens, Handbook of Experimental Pharmacology, vol. 135/I, Springer, Berlin, Heidelberg, 1999, pp. 315–328]. Most of the neurotropic effects of estrogens are related to transcriptional regulation of target genes; this regulation is induced by activating estrogen receptors in distinct neuronal areas.

The Estrogen Receptors

The estrogen receptor (ER) exists in two isoforms, ERα and ERβ, whose distribution and ligand-binding have been described [V. GIGUERE et al. (1998) Estrogen receptor β: re-evaluation of estrogen and anti-estrogen signaling; Steroids Vol. 63, pp 335–339 and G. G. KUIPER et al. (1997) The novel estrogen receptor subtype: potential role in the cell- and promoter-specific actions of estrogens and anti-estrogens, FEBS Lett, Vol. 410: pp 87–90]. The ligand-activated estrogen receptor binds to specific DNA sequences, called estrogen response elements (ERE), in the promoters of estrogen-responsive genes, thus influencing their transcription as a ligand-activated transcription factor. Both ER-isoforms are present in the brain and have distinct, not always overlapping, distribution in discrete and functionally different brain regions [P. J. Shughrue et al., Comparative distribution of estrogen receptor-a and -b mRNA in the rat central nervous system, J. Comp. Neurol., Vol. 388, pp. 507–525, 1997]. Upon binding of a natural or synthetic ligand, and before docking at EREs in order to influence transcription of target genes, the ER may recruit intrinsic co-activators and adapter proteins which serve as modulators (amplifiers or attenuators) of ER-mediated target gene transcription.

The Steroid Receptor Coactivator-1

The steroid receptor coactivator-1 (SRC-1) is a member of a family of cellular proteins which act as "amplifiers" of transcription mediated by nuclear receptors which are activated by ligand binding [S. A. Onate et al., Sequence and characterization of a coactivator for the steroid hormone receptor superfamily, Science, vol. 270, pp. 1354–1357, 1995]. SRC-1-mediated coactivation of estrogen receptor (ER) controlled transcription requires the presence of ER in agonistic conformation and involves the recruitment of additional mediators (e.g. CBP/p300). However, also autonomous activation domains have been identified [D. Robyr et al., Nuclear hormone receptor coregulators in action: Diversity for shared tasks, Mol. Endocrinol., vol.14, pp. 329–347, 2000].

SRC-1 is extensively expressed in estrogen target organs and estrogen-sensitive tumors [BERNS et al. (1998) Predictive value of SRC-1 for tamoxifen response of recurrent breast cancer, Breast Cancer Res. Treat. Vol. 48, 97–92, further NEWMANN et al. (2000) Cofactor competition between the ligand-bound estrogen receptor and an intron 1 enhancer leads to estrogen repression of ERBB2 expression in breast cancer, Oncogene, Vol 19, 490–497, and LABRIE et al., (1999) a third generation SERM acting as pure anti-estrogen in the mammary gland and endometrium, J. Steroid Biochem. Mol. Biol. Vol 69, 51–84]. If SRC-1 is inactivated by gene targeting, partial resistance to estrogens can be detected in several tissues, such as uterus, prostate, testis and mammary gland [XU et al. [1998] Partial hormone resistance in mice with disruption of the steroid receptor coactivator-1 (SRC-1) gene, Science, Vol. 279, 1922–1925]. However homozygous SRC-1 null-mutants failed to demonstrate alterations in brain functions in comparison to the natural phenotype. These results teach that SRC-1 may not play a role in modulating ER-mediated chemical signaling in the CNS. The publication of O. C. MEIJER, P. J. STEENBERGEN and E. R. DE KLOET (2000) Differential expression and regional distribution of steroid receptor coacitvators SRC-1 and SRC-2 in brain and pituitary, Endocrinology, Vol. 141, pp 2192–2199 describes two isoforms of SRC-1, namely SRC-1a and SRC-1e, in the adult rat brain distributed in distinct regions. SRC-1 is expressed in many brain areas, including hippocampus, amygdala, hypothalamus, basal ganglia and isocortex, which serve distinct functions with respect to either cognitive processing or regulation of reproduction-related functions, and are well-known for their sensitivity to estrogens.

Problem and Solutions

It is the problem of the invention to provide an in vitro screening for detecting estrogen receptor ligands which have estrogen-like effects in areas of the CNS having brain functions not related to reproduction. At the same time the ligands should not be effective in estrogen target organs other than the brain. Such estrogen receptor ligands, which are CNS selective, can be used for the prevention and therapy of disorders of the CNS caused by lack of estrogen. Such ligands will avoid the side-effects which estrogen administration has in the endometrium and breast and in the neuroendocrine control of gonadotropin secretion.

The problem of the invention is achieved by a method of an in vitro screening for a test substance (ligand) involving selecting and detecting by means of at least two assay systems comprising the following steps:

(i) in a first cellular or tissue assay system selecting the ligand having transcriptional activity
   which is mediated by activation of ER and which is measured by detecting potency in the cellular or tissue assay system comprising ER and an ER-driven reporter gene,
   whereby, in the first assay system, the ligand activates the potency with an $EC_{50(ER)}$ (half-maximally effective ligand concentration) lower than or equal to 10 nmol/l, and
   detecting the activation of the transcription; and
(ii) in a second cell-free or enzymatic assay system, selecting the physical-chemical interaction (recruitment) of SRC-1 and fragments thereof, and of the ER which is measured by detecting the potency of this interaction in the cell-free or enzymatic system
   wherein the ligand activates the ER and induces interaction with the co-present SRC-1 and fragments thereof in the second assay system with a $EC_{50(ER+SRC)}$ higher than or equal to 100 nmol/l, and detecting the potency of the physical-chemical interaction of SRC-1 and fragments thereof and of ER.

The expression fragments only stands for for NID 1, 2 or 3 (Nuclear inactivating domains), which are defined in:
Xiu Fen Ding, Carol M. Anderson, Han Ma, Heng Hong, Rosalie M. Uht, Peter J. Kushner and Michael R. Stallcup (1998) in Molecular Endocrinology 12 (2): 302–313 Copyright© 1998 by The Endocrine Society; Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities The sequence of the assay systems under (i) and (ii) is changeable. The assay system is such assay system which is preferably used first is an assay system which lead to the least number of positive selections or to least work. In all cases in which the estrogenic activity of a ligand is known, only the second assay system involving the combination of ER and co-activator SRC-1, has to be implemented.

The sequential use of the assay systems described under (i) and (ii) will allow the selection of preferred ligands, i.e. compounds which induce very little SRC-1 interaction(s) when measured in assay system (ii) at a defined concentration, in comparison to the dose required to produce half-maximal transcriptional activation in assay system (i).

In addition, the problem is achieved by a method of in vitro screening for a test substance (ligand),
   which is a known estrogen or a ligand with estrogenic activity, by in a cell-free or enzymatic assay system, selecting the physical-chemical interaction (recruitment) of SRC-1, and fragments thereof, and the ER, which is measured by detecting the potency of this interaction in the cell-free or enzymatic system,
   wherein the ligand activates the ER and induces interaction with the co-present SRC-1 and fragments thereof in the second assay system with a $EC_{50(ER+SRC)}$ higher than or equal to 100 nmol/l, and detecting the potency of the physical-chemical interaction of SRC-1 and fragments thereof, and ER.

Preference is given to a method of an in vitro screening for a test substance (ligand) according to the invention
   which ligand is an estrogen and transcriptionally activates a cellular assay system comprising ER and an ER-driven reporter gene,
   wherein the ligand activates the potency with an $EC_{50(ER)}$ (half-maximally effective ligand concentration) lower than or equal to 10 nmol/l.

Definitions in vivo: "In vivo techniques" stands for methods for treatment of human or animal body by surgery or therapy and diagnostic methods practised on the human or animal body.

in vitro: The expression "in vitro" excludes all in vivo techniques and methods mentioned above. The expression in vitro in this application furthermore means cultures, such as cell cultures, tissue cultures, parts of organs, organs, systems of organs and sections of parts of the animal body, especially the human body. All these specimens are removed from the animal or human organism. The specimen will not be re-introduced into the animal (including human) organism. Preference is given to the expression "in vitro", which stands for scientific and/or commercial experiments characterized by an artificial system using cells, fractions thereof, purified components or homogenates, outside of a living organism.

Ligands: The expression "ligand" will comprise all types of naturally occurring or synthetically produced chemical substance which are capable of binding ER, while not recruiting SRC-1 upon ER binding, and/or having a selective, neurotropic, estrogen-like transcription effect in central nervous system tissue and which have no biological effects on the tissues of the reproductive system. In this text, the ligand is the test substance.

Detection: The gene product of the estrogen response element can be identified by different systems, like ELISA, RIA, or enzymatic assay systems, in which the function of the product of the ERE is measured. Such methods are described in handbooks.

Cellular or tissue assay: This expression in this application furthermore means assays using cultures, such as cell cultures, tissue cultures, parts of organs, organs, systems of organs and sections of parts of the animal body, especially the human body.

Transcriptional activity and detection thereof: Transcriptional activity stands for the degree by which the amount of a mRNA encoding a defined protein changes as a result of an external (drug) influence on the promoter region of the corresponding gene.

The second assay system is based on the mechanism of co-activator-recruitment and only indirectly on transcription. The co-activator recruitment in this case stimulates the transcription, which can only be activated in the absence of a co-activator to a lower degree. In this invention, the core of the invention is the description of the cell-free or enzymatic assay system, in which the co-activator recruitment is measured without generating results about the transcription it self. The person skilled in the art is familiar with the fact that the assay system in presence of the co-activator SRC-1 self-evidently lead to an increase in transcription.

Such correlation between activation of ER-modulated transcription and co-activator-recruitment is described for example in WO 99/18124 from Cummings et al published on Apr. 15, 1999. Older methods are described in KAMEI et al. (1996) Cell Vol. 85, pages 403–414. Such methods involve, among other things, the construction of fusion proteins, the preparation of $^{32}$P-labeled proteins, the construction of specialized expression vectors, i.e. for the yeast two-hybrid assay and the transcriptional activation assays, the running of many gels, and the raising of antibodies. The methods take advantage of the ligand-dependent binding of nuclear receptors and co-activators. In the absence of ligand, binding between the nuclear receptor an the nuclear receptor co-activator does not occur. If ligand is present, however, such binding occurs and can be detected by fluorescence resonance energy transfer (FRET) between a fluorescently-labeled nuclear receptor and fluorescently-labeled nuclear receptor and fluorescently-labeled co-activator. Further ligands can be identified by virtue of their ability to prevent or disrupt to a different degree (or with a different potency) the agent-induced interaction of nuclear receptor co-activators. The nuclear receptor or ligand-binding domain thereof is labeled with a fluorescent reagent for use in the above-described methods of detecting ligands of nuclear receptors.

Potency: Potency is the value of the ligand-concentration as determined by the $EC_{50}$ (the dose required for half-maximal effect on a target parameter which is specifically influenced by a receptor bound to this ligand). The potency is primarily dependent on the affinity of the binding between individual ligands and the receptor as well as on ligand-induced conformational changes in the receptor protein which may alter the strength of the chemical signal transmission.

Control of ER: The control of ER is extensively described in the passage describing the state of the art.

Reporter gene: Genes or gene fragments which are linked or coupled to other genes or regulatory sequences in order to detect the activity of such sequences. Reporter genes have to produce gene products which are easily detectable. Furthermore, the gene products must not be toxic for the organisms which express these products. Reporter genes are described in Methods in Enzymol. Vol 152, pages 709–713 (1987). Further methods are described in WO 00/37681 from HARRIS et al. (published on Jun. 29, 2000) and WO 99/11760 from KUSHNER et al. (published on Mar. 11, 1999), which are both incorporated by reference.

Transcription: RNA-synthesis with the help of RNA-polymerase in the 5'→3'-direction using DNA as template. Transcription is the process of transferring the DNA sequence of one of the two DNA strands into a single-strand RNA sequence.

Activation of transcription: This term refers to the increase in ER-regulated/dependent reporter gene activity above the basal transcription rate which is observed in the absence of a ligand.

Regulation: Molecule having an effect on the transcription rate of the ER. Activation will comprise any higher transcription rate. Decrease stands for lowering of the transcription rate. The basal transcription rate is the value under conditions of absence of ligand, which conditions are comparable in the different assay systems (at least one assay system comprising the ER and the other assay system comprising ER together with SRC-1).

Cell-free system: For obtaining a cell-free system, the cell membranes or cell walls are destroyed, and cell membrane fragments and cell wall fragments are partially or completely removed for example by centrifugation, from the inner part of the cells (cytosol). Organic components contained in such cell compartments can maintain their capacity to enter biochemical interactions which are characteristic for the intact cell.

Enzymatic assay: In enzymatic assays, specific enzymes and, if necessary, cofactors are used to catalyze specific substrates. The changes in concentrations of substrates and products are measured. The enzymatic assays normally comprises a cascade of special enzymes and substrates.

Co-activator-recruitment: Recruitment of SRC-1 refers to the increase in the protein-protein interaction between ER and SRC-1 above the basal interaction rate measured in the absence of any ER-activating ligand.

Recruitment: Recruitment of SRC-1 relates to the comparison of the degrees of association by protein-protein interaction between co-present ER and SRC-1 in the absence or presence of an ER-agonist. Numerically, recruitment is defined by the molar concentration of ER-agonist which is required for the occurrence of a significant (more than 2 times standard deviation from baseline) protein-protein interaction between co-expressed ER and SRC-1 in a test system. The baseline is defined by the interaction measured in an identical test system to which no ER-antagonist has been added.

Advatages

The in vitro screening method based on the invention can select natural or synthetic compounds having specific neurotropic activity based on their ability to exert strong transcriptional activation through the ER without simultaneous strong recruitment of SRC-1. The screening method based on the invention precludes animal experimentation.

State of the art in vitro technologies for the identification of such ligands use surrogate parameters (such as elongation of neuronal processes, survival upon neurotoxic impact) which cannot predict dissociations between the systemic (e.g., uterotropic) and neurotropic efficacy of the ligands. A defined criterion for selective neurotropic efficacy of estrogen-related ligands is missing in the state of the art. Ligand selection depends on comparisons between systemic and neurotropic effects which make obligatory use of animals.

The obvious advantage of the invention is that animal tests are no longer necessary for finding ligands which do not feminize the animal or person taking the ligands.

In the state of the art at least one assay system using animals was necessary. The inventive step is supported by the comparison of the state of the art and assay results of the invention which surprisingly show differential expression of SRC-1 both in different parts of the brain and at different ages of individual development.

In the cortex, the following was found: The older the animal is, the lower is the SRC-1 presence in this brain region. Thus, there is little probability that estrogen receptor-mediated neuroprotection and repair involve recruitment of SRC-1 and amplification of ER signaling in this brain region.

In the ventromedial nucleus the following was found: The increasing presence of SRC-1 in critical phases of sexual maturation and in adulthood suggests that this co-activator supports ER signaling in this brain region in association with control of sexual function.

This differential expression throughout life has not been mentioned in the state of the art. Therefore, the screening method gives a sensitive technical tool for finding ligands which can be used for the treatment and prevention of neuro-degeneration in the cerebral cortex and is thus a useful method for the treatment and prevention of age-related cognitive disorders, affective disorders, Alzheimer's diseases and cerebral ischemia/stroke.

The ligands found by the inventive screening methods can be used for maintaining normal cell functions of the nervous system and preventing and treating pathological deterioration of theses functions.

Homozygous SRC-1 null-mutants do not have obvious alterations in brain function. [XU et al. (1998) Partial hormone resistance in mice with disruption of the steroid receptor coactivator-1 (SRC-1) gene, Science, Vol. 279, 1922–1925]; These results do not suggest that SRC-1 plays any role in modulating ER-mediated chemical signaling in the CNS.

C. MEIJER, P. J. STEENBERGEN and E. R. DE KLOET (2000), Vol. 141, pp 2192–2199, describes the distribution of SRC-1 in cells of different brain areas. Only rats of the same age were used for these experiments. The function of the SRC-1 expression in brain is not characterized by the authors. The test results disclose only the presence or absence of expression of SRC-1 in brain. The expression rate was not measured quantitatively. From this description, it cannot be deduced that SRC-1 may modulate any signal transmission by estrogen receptors in the nervous system in a region-specific context. The publication of MEIJER et al. is descriptive and does not involve quantification of the expression of SRC-1 in discrete brain regions, nor does it discuss the results in the context of ER-mediated signaling.

EXAMPLES

Example 1

Quantification of Regional Differences in the Expression of SRC-1 in Rat Brain During Postnatal Development Male and female Wistar rats were obtained from time-pregnant dams (Max Planck Institute of Psychiatry, Munich, Germany). Within the first 24 hours after delivery, litters were culled to 6 pups. The animals were housed under controlled illumination (light/dark 12/12 hours; lights on between 7:00 am and 7:00 pm), temperature (22–24° C.) and humidity (60 per cent) conditions, and had free access to standard laboratory diet and tap water. Upon weaning at the age of 22 days, rats were separated from their dams and grouped according to sex in colonies of 5. Timing of puberty in females was monitored by checking the vaginal opening and occurrence of cyclic changes in the vaginal epithelium, as determined by daily smears taken between the ages of 35 and 45 days.

Animals were sacrificed by decapitation at the following ages: day 1 (within 24 hours after birth), day 7, day 40 to 45 (at puberty, as defined in females) and day 90 (sexual maturity). Pubertal and sexually mature females were sacrificed at diestrus. Brains were removed from the skull (except for those of newborn rats) and snap-frozen in prechilled isopentane. The tissue was stored at −80° C. until sectioning. The experimental procedures were in compliance with regional and national regulations on animal welfare.

A 622-bases EcoRI fragment corresponding to bp 1125–1743 of the human SRC-1A cDNA (U90661) was purified and cloned into the vector pBS (Stratagene GmbH; Heidelberg, Germany). Upon amplification, sequence confirmation and linearization with appropriate restriction nucleases, cRNA were synthesized by in-vitro-transcription using T3 and T7 polymerases for antisense and sense probes, respectively. Radioactive labeling was obtained with $^{35}$S-UTP and -CTP (NEN Life Science Products GmbH; Cologne, Germany). Labeled cRNA was extracted by phenol/chloroform/isoamyl alcohol and purified on Nuctrap columns (Stratagene). The specific activity of the probes used exceeded $10^6$ cpm/μl.

Coronal cryosections of 15 μm thickness containing the medial preoptic nucleus (MPN) and hypothalamic ventromedial nucleus (VMN) were obtained from adult rat brains at the level of bregma −0.51 and −2.45 mm, respectively [L. W. Swanson, Brain maps: Structure of the rat brain; Elsevier, Amsterdam, 1998]. In pubertal, juvenile and newborn animals, samples containing the two regions of interest were selected from serial rostro-caudal sections. The sections of the VMN also contained the rostral part of the hippocampal formation and the amygdaloid nuclear complex. Sections were mounted on gelatine-coated slides. Fixation, permeabilization, hybridization with $^{35}$S-labeled probes and stringency washing were performed according to a standardized protocol [H. J. Whitfield et al., Optimization of cRNA probe in situ hybridization methodology for localization of glucocorticoid receptor mRNA in rat brain: A detailed protocol. Cell. Mol. Neurobiol., vol. 10, pp. 145–157, 1990]. Non-specific hybridization signals were monitored by hybridizing control sections from each age group with the sense probe. Autoradiographs were generated by exposure to Hyperfilm βmax (Amersham; Braunschweig, Germany) for 14 days.

Film autoradiographs were assessed by computer-assisted densitometry (NIH Image 5.1; National Institute of Mental Health, Bethesda, USA). Four measurements of the optical density (gray level) of the area of interest with automatic background subtraction were performed in two adjacent sections from each individual. In all age groups, signal densities were measured in squares (cerebral cortex, MPN and VMN) or strips (hippocampal subfield CA1) of identical size, in order to avoid bias resulting from age-associated changes in the dimension of these structures. Individual average optical density values were used for the computation of specific signal radioactivity (μCi/g tissue) by means of a third-order polynomial equation resulting from measurements of co-exposed $^{14}$C standards (ARC; St. Louis, USA). Group means were compared by one-way ANOVA; where appropriate, pairwise comparisons were performed by the Student-Neuman-Keuls test. The level of significance was pre-set at $p<0.05$.

At the anatomical levels examined, distinct strong specific hybridization signals were found in the dentate gyrus and the CA-subfields of the hippocampal formation; the medial preoptic, ventromedial and arcuate nuclei, the cingulate, parietal and temporal cortex, and the amygdaloid nuclear complex all displayed moderate signal intensity. Incubation with a labeled sense probe failed to provide a specific hybridization signal in any structure or age group.

Among all the structures investigated, in newborn animals, the cerebral cortex displayed the highest density of SRC-1a-encoding transcripts. Within the first postnatal week, a significant decrease in signal intensity was measured; the declining trend continued with increasing age, resulting in adult levels of approximately 30 per cent of those measured at birth. At any age investigated, SRC-1a expression in the brain cortex failed to display gender differences (see Table I).

TABLE I

| Age (days) | Cerebral cortex male | Cerebral cortex female | stage of life |
|---|---|---|---|
| 1 | 0.68 ± 0.10 | 0.56 ± 0.03 | birth |
| 7 | 0.32 ± 0.07 | 0.38 ± 0.01 | youth |
| 40 | 0.27 ± 0.01 | 0.27 ± 0.01 | puberty |
| 90 | 0.23 ± 0.01 | 0.24 ± 0.01 | sexual maturity |

These results suggest that amplification of ER-mediated signaling by co-present SRC-1 in the cerebral cortex, a structure which is crucial for cognitive performance, abruptly decreases and, probably, loses functional importance with increasing age. Furthermore, these data suggest that, once early brain development (encompassing neurogenesis, neuronal growth and synaptic connectivity) is accomplished, recruitment of SRC-1 by activated ER plays a negligible role in the mediation of estrogen effects in the cerebral cortex. With respect to the functional specificity of this brain area (cognitive processing), it appears unlikely that SRC-1 recruitment should have significant importance for the manifestation of estrogen effects on this brain function.

Opposite developmental dynamics of SRC-1 expression were seen in the hypothalamic ventromedial nucleus (VMN), a brain area which is richly endowed with ER and has major importance in the control of reproductive functions and sexual behavior by estrogens. At birth, SRC-1a hybridization signals in the VMN were modest in both sexes. Within the first postnatal week significant increases in transcript densities were documented and, in both sexes, peak signal intensities in this structure were measured around puberty (see Table II)

TABLE II

| Age (days) | Ventromedial nucleus male | Ventromedial nucleus female | stage of life |
|---|---|---|---|
| 1 | 0.27 ± 0.03 | 0.25 ± 0.01 | birth |
| 7 | 0.33 ± 0.01 | 0.31 ± 0.01 | youth |
| 40 | 0.43 ± 0.01 | 0.37 ± 0.01 | puberty |
| 90 | 0.38 ± 0.02 | 0.30 ± 0.02 | sexual maturity |

These results indicate that the presence and, probably, recruitment of SRC-1 represent a necessary pre-condition for the transmission of chemical signals through activation of the ER in a brain region which regulates reproduction-related endocrine activity and behavior. This conclusion is corroborated by the fact that SRC-1 expression in the VMN is abruptly increased in phases of life in which there are dramatic transitions in the reproductive system, e.g., puberty data on day 40 in Table II) and during the estrous cycle (Table II).

TABLE III

| Phase of ovarian cycle | Expression level in the VMN | Expression level in the cerebral cortex |
|---|---|---|
| Diestrus | 0.43 ± 0.02 | 0.32 ± 0.03 |
| Proestrus | 0.60 ± 0.04 | 0.38 ± 0.02 |

Example 2

Assay for the Quantitative Determination of SRC-1 Recruitment by the Activated ER and Differential Behavior of ER Ligands in this Assay The assay employed in this Example only used compounds which are characterized by estrogenic activity. The assays for finding the estrogenic compounds have already been developed and published. These assays are standard assays well known to the person skilled in the art.

The assay used in the present Example for investigating the recruitment of ER and co-activator SRC-1 is performed according to the publication of Gauchao ZHOH et al. (1998) Nuclear receptors have distinct affinities for co-activators: Characterization by fluorescence resonance energy transfer, Mol Endo, Vol 12, pp 1594–1604 especially on Page 1602. Furthermore, the assaysystem is described in WO/18124 from Cummings et al. Instead of the euriopium cryptate, mentioned in the International Application, europium chelate—100 ng of euriopium labeled anti-GST-antibody per well—is used in the assays. The labeled antibody was delivered from Wallac, now Perkin Elmer Lifesciences. (Eu-W1024 labeled anti-GST-Antibody for Lance Assays, Part Number AD 0065)

The SRC-1 is used at a concentration of 175 ng his-tagged SRC-1 per well. SRC-1 is present in every well of this assay system.

Using the assay system, the following results can be determined:

The control containing the natural estrogen 17β-estradiol [i] shows significant interaction between ER and SRC-1 at $10^{-9}$ M.

The synthetic estrogens (ent-1,3,5(10)-estratriene-3,17β-diol) [ii], (3',15β-dihydrocycloprop[14,15]-estra-1,3,5(10),8-tetraene-3,17α-diol) [iii], (15β-allyl-estra-1,3,5,(10)-triene-3,17β-diol) [iv] and (15β-propyl-estra-1,3,5,(10)-triene-3,17β-diol) [v]

were subjected to comparative testing in the system described above. The results of the comparison are presented in the following Table IV.

The results demonstrate that synthetic compounds which display similar agonistic activity in ER-mediated transcriptional regulation show substantial differences with respect to their ability to recruit co-present SRC-1 upon binding to the ER. The calculated ratios between the values obtained in the two assay systems allow the identification of ER ligands with differential ability to engage SRC-1 in transcriptional regulation. ER agonists with selective neurotropic properties are those which show higher ratios between the values determined in assay system II (recruitment of ER and co-activator SRC-1) and assay system I (ER).

TABLE IV

| Ligand | Assay system I: Transcriptional activation of an ER-dependent reporter gene ($EC_{50}$ in M) | Assay system II: First signs of significant interaction between ER and SRC-1 protein (dose in M) | Ratio between values measured in assay systems II and I |
|---|---|---|---|
| [i] | $6.10^{-11}$ | $10^{-9}$ | 16.6 |
| [ii] | $4.10^{-9}$ | $10^{-8}$ | 2.5 |
| [iii] | $1.10^{-9}$ | $10^{-7}$ | 100.0 |

TABLE IV-continued

| Ligand | Assay system I: Transcriptional activation of an ER-dependent reporter gene ($EC_{50}$ in M) | Assay system II: First signs of significant interaction between ER and SRC-1 protein (dose in M) | Ratio between values measured in assay systems II and I |
|---|---|---|---|
| [iv] | $4 \cdot 10^{-9}$ | $10^{-7}$ | 25.0 |
| [v] | $1 \cdot 10^{-8}$ | $10^{-7}$ | 10.0 |

Example 3

Demonstration of Selective Neurotropic Activity by ER Ligands Identified by their Failure to Recruit SRC-1 Upon ER Binding Using the assay described in Example 2, we selected the compound 3' 15β-dihydrocycloprop[14,15]estra-1,3,5(10),8-tetraene-3,17α-diol [iii] for further examination of its neurotropic and systemic estrogenic effects. The compound was shown to bind to ERα and ERβ with a relative affinity of 25–30 per cent of that of the natural ER ligand 17β-estradiol [i]. Furthermore, the compound demonstrated measurable activation of the transcription of an ER-inducible reporter gene in vitro, with an EC50 of $10^{-9}$ M (17β-estradiol displayed EC50 of $10^{-10}$ M).

Different doses of the compound of interest and the reference 17β-estradiol were administered subcutaneously in ovariectomized female rats for seven consecutive days. The effect of the compounds on the cognitive performance of experimental animals was evaluated by monitoring the acquisition, consolidation and retrieval of active avoidance behavior. Upon sacrifice, morphometric assessment was made of estrogen-sensitive organs (uterus, thymus, adrenal glands). Neurochemical effects were assessed by quantification of the transcription of ER-induced CNS-specific genes in different brain areas, endowed with different amounts of SRC-1.

In summary, the results indicate that
- the capacity of 3',15β-dihydrocycloprop[14,15]estra-1,3,5(10),8-tetraene-3,17α-diol [iii], to induce estrogen-like effects in peripheral estrogen-target organs (uterus, thymus, adrenal glands) is several times lower than that of the natural estrogen 17β-estradiol, which also strongly recruits SRC-1 upon ER binding;
- the compound 3',15β-dihydrocycloprop[14,15]estra-1,3,5(10),8-tetraene-3,17α-doil [iii] stimulates the transcription of the antiapoptotic estrogen-regulated gene bcl-2 in the cerebral cortex (a brain area with poor expression of SRC-1) to a higher degree than does 17β-estradiol given at an equal dose;
- the compound 3',15β-dihydrocycloprop[14,15]estra-1,3,5(10),8-tetraene-3,17α-diol [iii] induces the estrogen-dependent expression of oxytocin receptors in the SRC-1-rich and reproduction-relevant ventromedial nucleus (VMN) to a significantly lower degree than 17β-estradiol;
- the behavioral (cognitive) effect of the compound 3',15β-dihydrocycloprop[14,15]estra-1,3,5(10),8-tetraene-3,17α-diol, as measured by retention of newly acquired active avoidance behavior is indistinguishable from that of 17β-estradiol [i]; however, this behavioral efficacy was not associated with estrogen-dependent changes in peripheral estrogen-sensitive organs.

The results summarized above suggest that a compound, which
- displays measurable affinity for the ER,
- acts as an agonist of the ER with regard to transcriptional regulation of estrogen-dependent genes, and
- fails to recruit SRC-1 upon binding to the ER in vitro acts as a selective neurotropic estrogen in vivo, while negligibly affecting peripheral estrogen target organs.

The invention claimed is:

1. A method of screening a group of test substances for one or more ligands to be administered as effective ingredients in a method of treating neuro-degeneration, said test substances being selected from the group consisting of estrogens and compounds having estrogen activity, said method of screening comprising the steps of:
   a) providing a cell-free or enzymatic assay system for each of said test substances, said cell-free or enzymatic assay system comprising an estrogen receptor for said test substances and a co-present steroid receptor coactivator-1, and fragments thereof;
   b) experimentally determining half-maximally effective ligand concentrations ($EC_{50(ER+SRC)}$) for each of said test substances at which a physical-chemical interaction of said co-present steroid receptor coactivator-1, and said fragments thereof, and said estrogen receptor occurs in the cell-free or enzymatic system in the presence of each of said test substances;
   c) selecting said one or more of said test substances if said half-maximally effective ligand concentration ($EC_{50(ER+SRC)}$) for said one or more of said test substances is greater than or equal to 100 nmol/l;
   d) providing a cellular or tissue assay system comprising an estrogen receptor and an estrogen receptor-driven reporter gene;
   e) experimentally determining half-maximally effective ligand concentrations ($EC_{50(ER)}$) for said one or more test substances selected during the selecting of step c) at which said cellular or tissue assay system is transcriptionally activated in the presence of said one or more test substances; and
   f) selecting those of said one or more test substances having said half-maximally-effective ligand concentrations that transcriptionally activate said cellular or tissue assay system and that are less than or equal to 10 nmol/l as said one or more ligands for said method of treating said neuro-degeneration.

2. A method of screening a group of test substances for one or more ligands to be administered as effective ingredients in a method of treating neuro-degeneration, said test substances being selected from the group consisting of estrogens and compounds having estrogen activity, said method of screening comprising the steps of:
   a) providing a cell-free or enzymatic assay system for each of said test. substances, said cell-free or enzymatic assay system comprising an estrogen receptor for said test substances and a co-present steroid receptor coactivator-1, and fragments thereof;
   b) experimentally determining half-maximally effective ligand concentrations ($EC_{50(ER+SRC)}$) for each of said test substances at which a physical-chemical interaction of said co-present steroid receptor coactivator-1, and said fragments thereof, and said estrogen receptor occurs in the cell-free or enzymatic system in the presence of each of said test substances;
   c) selecting said one or more of said test substances if said half-maximally effective ligand concentration ($EC_{50(ER+SRC)}$) for said one or more of said test substances is greater than or equal to 100 nmol/l d) providing a cellular or tissue assay system comprising an estrogen receptor and an estrogen receptor-driven reporter gene;

e) experimentally determining half-maximally effective ligand concentrations ($EC_{50(ER)}$) for said one or more test substances selected during the selecting of step c) at which said cellular or tissue assay system is transcriptionally activated in the presence of said one or more test substances; and f) selecting those of said one or more test substances having said half-maximally-effective ligand concentrations that transcriptionally activate said cellular or tissue assay system and that are less than or equal to 10 nmol/l as said one or more ligands for said method of treating said neuro-degeneration;

wherein said neuro-degeneration is an age-related cognitive disorder, affective disorder, Alzheimer's disease or cerebral ischemia/stroke.

* * * * *